(12) United States Patent
Ou et al.

(10) Patent No.: US 7,683,233 B2
(45) Date of Patent: Mar. 23, 2010

(54) PROCESS FOR PRODUCING PARA-XYLENE

(75) Inventors: John Di-Yi Ou, Houston, TX (US); Sebastian C. Reyes, Branchburg, NJ (US); Bal K. Kaul, Fairfax, VA (US); Wenyih Frank Lai, Bridgewater, NJ (US); Brenda A. Raich, Annandale, NJ (US); Charanjit S. Paur, Roselle Park, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 457 days.

(21) Appl. No.: 11/894,187

(22) Filed: Aug. 20, 2007

(65) Prior Publication Data

US 2008/0071126 A1    Mar. 20, 2008

Related U.S. Application Data

(60) Provisional application No. 60/844,430, filed on Sep. 14, 2006.

(51) Int. Cl.
C07C 7/13    (2006.01)

(52) U.S. Cl. .................... 585/828; 585/820; 585/827

(58) Field of Classification Search .................. None
See application file for complete search history.

(56) References Cited

U.S. PATENT DOCUMENTS

| | | | |
|---|---|---|---|
| 2,775,628 A | 12/1956 | Nicholson et al. | |
| 3,662,013 A | 5/1972 | Machell et al. | |
| 3,706,812 A | 12/1972 | Derosset et al. | |
| 3,732,325 A | 5/1973 | Pharis et al. | |
| 3,773,846 A | 11/1973 | Berger | |
| 3,813,452 A | 5/1974 | Bieser | |
| 3,939,221 A | 2/1976 | Pearce | |
| 3,997,620 A | 12/1976 | Neuzil | |
| 4,120,911 A | 10/1978 | Davidson | |
| 4,188,282 A | 2/1980 | Tabak et al. | |
| 4,211,886 A | 7/1980 | Tabak et al. | |
| 4,236,996 A | 12/1980 | Tabak et al. | |
| 4,439,535 A * | 3/1984 | Smolin et al. ................. | 502/62 |
| 4,886,929 A | 12/1989 | Neuzil et al. | |
| 6,004,452 A | 12/1999 | Ash et al. | |
| 6,074,457 A * | 6/2000 | Anthonis et al. ............... | 95/45 |
| 6,376,733 B1 | 4/2002 | Ferraro et al. | |

(Continued)

FOREIGN PATENT DOCUMENTS

WO    2005/054161    6/2005

(Continued)

*Primary Examiner*—Tam M Nguyen

(57) ABSTRACT

In a process for producing a para-xylene enriched product from a gaseous mixture comprising at least para-xylene, meta-xylene and ortho-xylene, the gaseous mixture is contacted with an adsorbent capable of selectively adsorbing para-xylene and comprising a crystalline molecular sieve having an average crystal size between about 0.5 micron and about 20 microns. The contacting is conducted at a temperature and pressure such that at least part of the para-xylene in the mixture is adsorbed by the adsorbent to produce a para-xylene-depleted effluent stream. The para-xylene is then desorbed from said adsorbent and collected to form a para-xylene enriched stream. The adsorption and desorption steps are repeated for a plurality of cycles, such that the time between successive contacting steps is no more than 10 seconds.

17 Claims, 8 Drawing Sheets

U.S. PATENT DOCUMENTS

| | | |
|---|---|---|
| 6,376,734 B1 | 4/2002 | Magne-Drisch et al. |
| 6,376,736 B1 | 4/2002 | Rutten et al. |
| 6,600,083 B2 | 7/2003 | Doyle et al. |
| 6,689,929 B2 | 2/2004 | Williams et al. |
| 6,841,714 B2 | 1/2005 | Leflaive et al. |
| 6,878,855 B2 | 4/2005 | Deckman et al. |
| 7,381,858 B2 * | 6/2008 | Huff et al. .................. 585/805 |
| 2004/0010170 A1 * | 1/2004 | Vickers ...................... 585/319 |
| 2004/0220047 A1 * | 11/2004 | Doyle et al. .................. 502/71 |
| 2004/0220439 A1 * | 11/2004 | Williams et al. ............ 585/477 |
| 2005/0167338 A1 | 8/2005 | Miller et al. |
| 2005/0171395 A1 | 8/2005 | Huff, Jr. et al. |

FOREIGN PATENT DOCUMENTS

| | | |
|---|---|---|
| WO | 2005/075389 | 8/2005 |
| WO | 2005/075390 | 8/2005 |

* cited by examiner

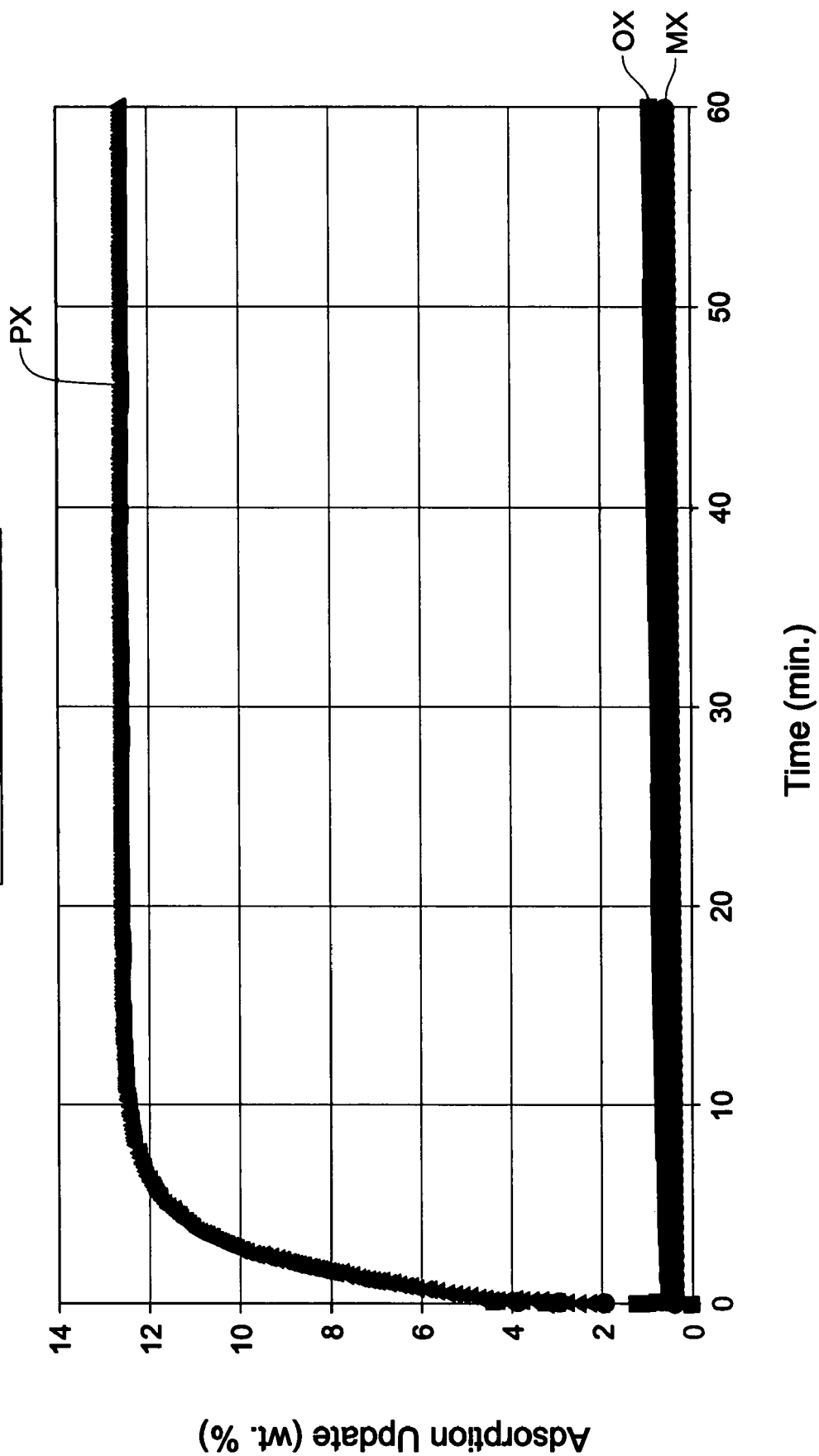

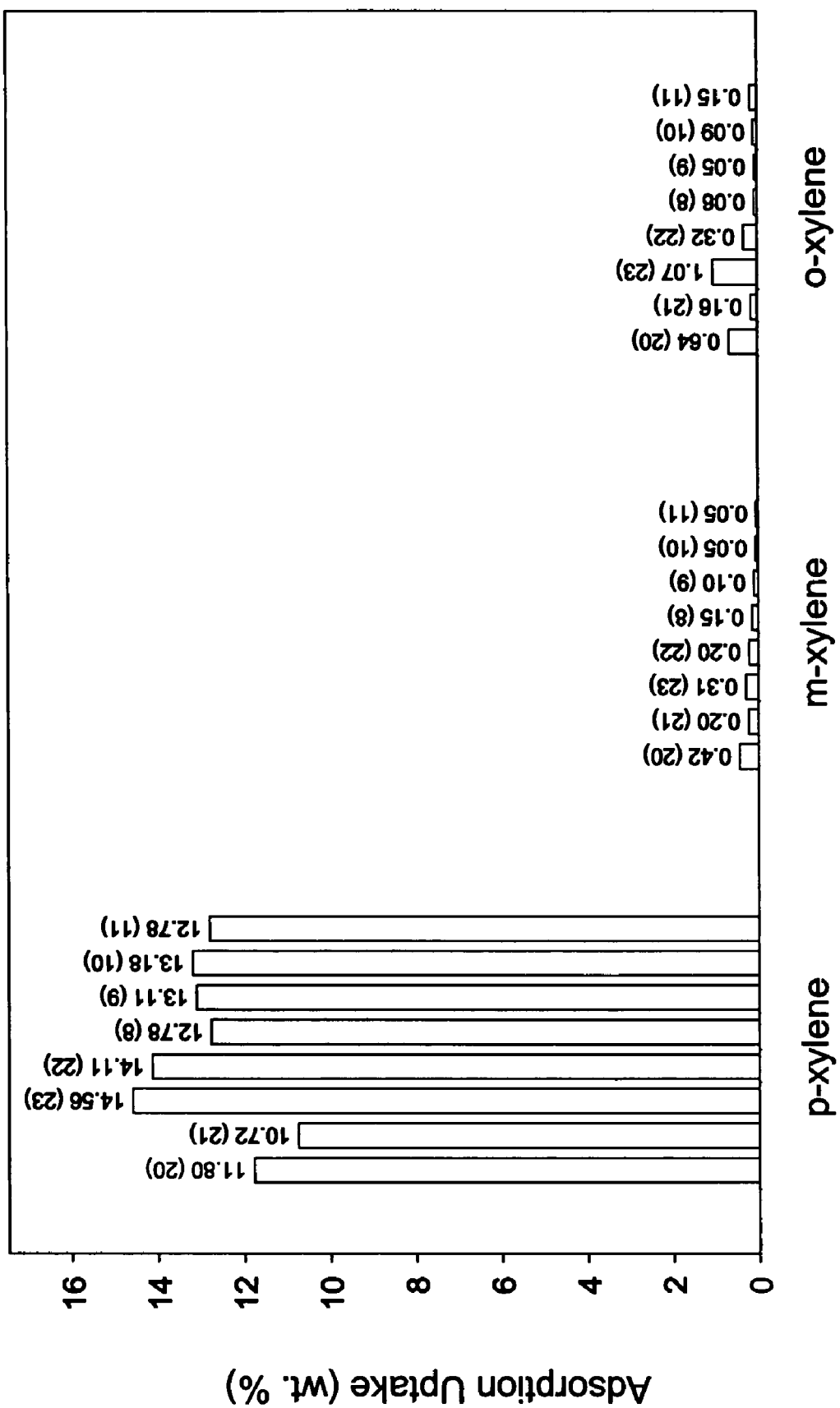

PROCESS FOR PRODUCING PARA-XYLENE

CROSS REFERENCE TO RELATED APPLICATIONS

This application claims priority from U.S. Provisional Patent Application Ser. No. 60/844,430, filed Sep. 14, 2006, the entire contents of which are incorporated herein by reference.

FIELD

This invention relates to a process for producing para-xylene.

BACKGROUND

Ethylbenzene (EB), para-xylene (PX), ortho-xylene (OX) and meta-xylene (MX) are often present together in $C_8$ aromatic product streams from chemical plants and oil refineries. Of these $C_8$ compounds, although EB is an important raw material for the production of styrene, for a variety of reasons most EB feedstocks used in styrene production are produced by alkylation of benzene with ethylene, rather than by recovery from a $C_8$ aromatics stream. Of the three xylene isomers, PX has the largest commercial market and is used primarily for manufacturing terephthalic acid and terephthalate esters for use in the production of various polymers such as poly (ethylene terephthalate), poly(propylene terephthalate), and poly(butene terephthalate). While OX and MX are useful as solvents and raw materials for making products such as phthalic anhydride and isophthalic acid, market demand for OX and MX and their downstream derivatives is much smaller than that for PX.

Given the higher demand for PX as compared with its other isomers, there is significant commercial interest in maximizing PX production from any given source of $C_8$ aromatic materials. However, there are two major technical challenges in achieving this goal of maximizing PX yield. Firstly, the four $C_8$ aromatic compounds, particularly the three xylene isomers, are usually present in concentrations dictated by the thermodynamics of production of the $C_8$ aromatic stream in a particular plant or refinery. As a result, the PX production is limited, at most, to the amount originally present in the $C_8$ aromatic stream unless additional processing steps are used to increase the amount of PX and/or to improve the PX recovery efficiency. Secondly, the $C_8$ aromatics are difficult to separate due to their similar chemical structures and physical properties and identical molecular weights.

A variety of methods are known to increase the concentration of PX in a $C_8$ aromatics stream. These methods normally involve recycling the stream between a separation step, in which at least part of the PX is recovered to produce a PX-depleted stream, and a xylene isomerization step, in which the PX content of the PX-depleted stream is returned back towards equilibrium concentration, typically by contact with a molecular sieve catalyst. However, the commercial utility of these methods depends on the efficiency, cost effectiveness and rapidity of the separation step which, as discussed above, is complicated by the chemical and physical similarity of the different $C_8$ isomers.

Fractional distillation is a commonly used method for separating different components in chemical mixture. However, it is difficult to use conventional fractional distillation technologies to separate EB and the different xylene isomers because the boiling points of the four $C_8$ aromatics fall within a very narrow 8° C. range, namely from about 136° C. to about 144° C. (see Table 1 below). In particular, the boiling points of PX and EB are about 2° C. apart, whereas the boiling points of PX and MX are only about 1° C. apart. As a result, large equipment, significant energy consumption, and/or substantial recycles would be required for fractional distillation to provide effective $C_8$ aromatic separation.

TABLE 1

| $C_8$ Compound | Boiling Point (° C.) | Freezing Point (° C.) |
|---|---|---|
| Ethylbenzene (EB) | 136 | −95 |
| Para-xylene | 138 | 13 |
| Meta-xylene | 139 | −48 |
| Ortho-xylene | 144 | −25 |

Fractional crystallization is an alternative method of separating components of a mixture and takes advantage of the differences between the freezing points and solubilities of the components at different temperatures. Due to its relatively higher freezing point, PX can be separated as a solid from a $C_8$ aromatic stream by fractional crystallization while the other components are recovered in a PX-depleted filtrate. High PX purity, a key property needed for satisfactory conversion of PX to terephthalic acid and terephthalate esters, can be obtained by this type of fractional crystallization. U.S. Pat. No. 4,120,911 provides a description of this method. However, fractional crystallization is slow and the need to avoid the formation of binary eutectics between PX and MX and between PX and OX limits the amount of PX that can removed per pass through the crystallizer.

An alternative xylene separation method uses molecular sieves, such as zeolites, to selectively adsorb para-xylene from the $C_8$ aromatic feedstream to form a PX-depleted effluent. The adsorbed PX can then be desorbed by various ways such as heating, lowering the PX partial pressure or stripping. For example, U.S. Pat. No. 3,997,620 discloses a process for separating para-xylene from a feed stream comprising para-xylene and at least one other $C_8$ aromatic isomer which process comprises the steps of: (a) contacting said feed stream at adsorption conditions with an adsorbent comprising type X or type Y zeolite containing barium and strontium in a weight ratio of barium to strontium of from about 1:1 to about 15:1 at the exchangeable cationic sites to effect the selective adsorption of para-xylene; (b) removing a raffinate component comprising a less selectively adsorbed $C_8$ aromatic from said adsorbent; (c) contacting said adsorbent with a desorbent material comprising para-diethylbenzene at desorption conditions to effect the desorption of para-xylene from said adsorbent; and, (d) removing from said adsorbent an extract component comprising para-xylene.

Similarly, U.S. Pat. No. 4,886,929 discloses a process for separating the para-isomers of a dialkyl-substituted aromatic hydrocarbon from a mixture of said para-isomer and at least one other isomer of said aromatic hydrocarbon, which process comprises contacting said mixture with a crystalline aluminosilicate adsorbent, particularly zeolite X or Y, containing barium and potassium at exchangeable cationic sites within the adsorbent crystalline structure in a $BaO/K_2O$ molar ratio of from about 0.6 to 1.2 at adsorption conditions selected to effect the adsorption of said para-isomer by said adsorbent and subsequently contacting said adsorbent with a desorbent material selected from meta-difluorobenzene and ortho-difluorobenzene and mixtures thereof at desorption conditions to effect the removal of said para-isomer from said adsorbent and recovering from said adsorbent a stream concentrated in said para-isomer.

Two commercially available xylene separation processes used in many chemical plants or refineries are the PAREX™ and ELUXYL™ processes. Both of these processes use molecular sieves to adsorb PX. In such molecular-sieve based adsorption processes, a higher amount of PX, typically over 90%, compared with that from a fractional crystallization process, typically below 65%, may be recovered from the PX present in a particular feed. Although this improved recovery is a significant advantage, it is accompanied by significant disadvantages, including a complex and expensive process scheme, large equipment sizes (up to 1 million pounds of adsorbent required) and high energy consumption. As a result the PX adsorption unit is generally the rate-limiting step in most PX production plants.

In addition to large pore molecular sieves, such as zeolite X and Y, attempts have been made to use adsorption with medium pore zeolites, such as ZSM-5 and ZSM-11, to separate PX from mixtures of C8 aromatics. However, a major disadvantage of these processes is that the time required to effect desorption of the adsorbed components is too long to provide a commercially useful process. In addition, with acidic zeolites, such as HZSM-5, the high temperatures used to obtain rapid desorption cause catalytic reactions to occur converting PX to MX and OX and converting EB to benzene. Furthermore, with HZSM-5, traces of olefins, which are usually present in commercial feeds, irreversibly chemisorb lowering the adsorption capacity of the zeolite. As a result, frequent reconditioning of the adsorbent (e.g., removal of coke deposits) is required.

In an attempt to avoid these problems, various proposals have been made to employ pressure swing adsorption at elevated temperature and pressure with a non-acidic, molecular sieve-containing adsorbent, such as silicalite, to selectively adsorb PX and EB from mixtures of $C_8$ aromatics. Desorption is said to be significantly faster and reactions of the adsorbed molecules (PX and EB) do not occur. In addition, olefins do not adsorb irreversibly on the silicalite, so the adsorption capacity of the adsorbent remains high and frequent reconditioning is not required.

For example, U.S. Pat. No. 6,689,929 discloses a pressure swing adsorption process for separating para-xylene and ethylbenzene from a $C_8$ aromatics stream produced by toluene conversion. The process uses a para-selective adsorbent, preferably orthorhombic crystals of silicalite having an average minimum dimension of at least about 0.2 μm, and is operated isothermally in the vapor phase at elevated temperatures and pressures. Para-xylene and ethylbenzene are preferentially adsorbed in a fixed bed of the adsorbent and, when the bed is saturated with para-xylene and ethylbenzene, the feed to the process is stopped and the partial pressure is lowered to desorb the para-xylene and ethylbenzene. A stream of non-adsorbed meta-xylene and ortho-xylene may be obtained before desorbing the para-xylene and ethylbenzene. Cycle times, that is the time between successive sorption/desorption cycles, of between 2 minutes and 200 minutes are disclosed.

In addition, U.S. Pat. No. 6,878,855 discloses a process for producing a para-xylene enriched product from a feedstream comprising xylenes and ethylbenzene, wherein the process comprises: (a) passing the feedstream through at least one isomerization reactor containing an isomerization catalyst to isomerize the xylenes and at least partially isomerize and/or at least partially destroy the ethylbenzene present in the feedstream to form an isomerization effluent; and (b) feeding the isomerization effluent in vapor phase through at least one swing adsorption unit containing a sorbent to produce alternately, at a cycle time, an exiting raffinate comprising a para-xylene depleted stream during an adsorption mode and a desorption effluent comprising the para-xylene enriched product during a desorption mode. Suitable adsorbents for use in the swing adsorption unit include zeolitic and non-zeolitic molecular sieves, especially medium pore zeolites having a pore diameter of smaller than about 7 Å, such as MFI type zeolites, for example ZSM-5 and silicalite, and pillared clays, carbons, and mixtures thereof. Suitable cycle times are said to be from about 0.1 second to about 120 minutes.

It is appreciated that swing adsorption of para-xylene from a mixed $C_8$ aromatic feedstream is a cost-effective way of increasing the PX concentration in the feedstream. By increasing the PX concentration in the feedstream, swing adsorption can provide an inexpensive way of increasing the efficiency of a downstream separation unit, which could be a conventional PAREX™, ELUXYL™ or crystallization unit, and thereby assist in debottlenecking the xylenes loop in an aromatics complex. The present invention seeks to provide an improved swing adsorption process for recovering PX and an improved xylene production process incorporating swing adsorption of PX.

SUMMARY

In one aspect, the invention resides in a process for producing a para-xylene enriched product from a gaseous mixture comprising at least para-xylene, meta-xylene and ortho-xylene, the process comprising:

(a) contacting the gaseous mixture with an adsorbent capable of selectively adsorbing para-xylene and comprising a crystalline molecular sieve having an average crystal size between about 0.5 micron (μm) and about 20 microns, such as between about 1 micron and about 10 microns, typically between about 1 micron and about 5 microns, said contacting being conducted at a temperature and pressure such that at least part of the para-xylene in the mixture is adsorbed by the adsorbent to produce a para-xylene-depleted effluent stream; then (b) desorbing para-xylene from said adsorbent;

(c) collecting the desorbed para-xylene to form a para-xylene enriched stream; and (d) repeating (a) and (b) for a plurality of cycles, wherein the time between successive contacting steps is no more than 10 seconds, typically no more than 5 seconds.

Conveniently, the crystalline molecular sieve comprises a material having a structure type selected from MFI, MEL, TON, MTT, MFS, MWW, FER, EUO, AEL, ITH and AFO. Preferably, the molecular sieve is an MFI material. The MFI molecular sieve can have crystals of either a spherical shape morphology or a coffin shape morphology, or mixture thereof. Generally, the crystalline molecular sieve comprises an aluminosilicate having a silica to alumina molar ratio of 100 to 500.

In one embodiment, para-xylene is desorbed from said adsorbent by decreasing the partial pressure of para-xylene.

Conveniently, at least part of the para-xylene-depleted effluent stream is passed to a xylene isomerization unit to increase the para-xylene content thereof and produce a second effluent stream.

In one embodiment, at least part of the para-xylene enriched stream and/or the second effluent stream is subjected to a further para-xylene separation step. Conveniently, said further para-xylene separation step comprises crystallization, selective adsorption and/or membrane separation. In one embodiment, said further para-xylene separation step comprises:

(a) contacting the stream with a further adsorbent capable of selectively adsorbing para-xylene such that at least part of the para-xylene in the stream is adsorbed by the adsorbent to produce a further para-xylene-depleted effluent stream; then (b) desorbing para-xylene from said further adsorbent;
(c) collecting the desorbed para-xylene to form a further para-xylene enriched stream; and
(d) repeating (a) and (b) for a plurality of cycles, wherein the time between successive contacting steps is greater than 10 seconds.

Conveniently, the further para-xylene-depleted effluent stream is passed to a further xylene isomerization unit to increase the para-xylene content thereof and produce a third effluent stream.

Conveniently, the gaseous mixture comprising at least para-xylene, meta-xylene and ortho-xylene comprises at least part of the third effluent stream.

DETAILED DESCRIPTION OF THE EMBODIMENTS

Figure 1:
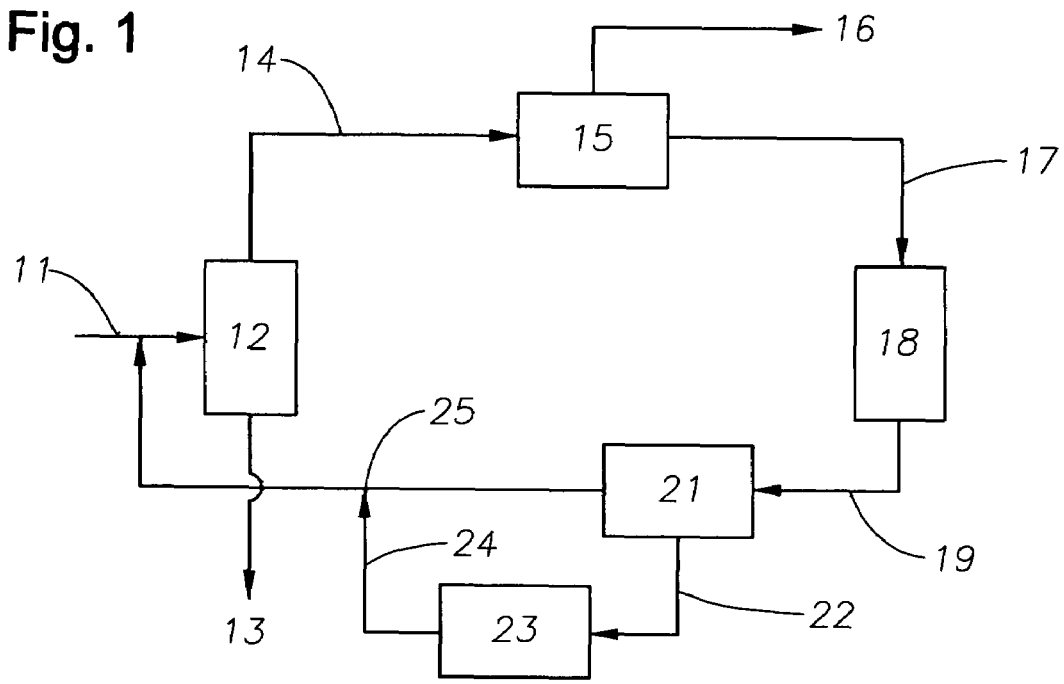
FIG. 1 is a flow diagram of a para-xylene production process according to one embodiment of the present invention.

The present invention provides a process for producing a para-xylene enriched product from a gaseous mixture comprising at least para-xylene, meta-xylene and ortho-xylene, in which the mixture is fed to a swing adsorption unit employing an adsorbent capable of selectively adsorbing para-xylene and comprising a crystalline molecular sieve having an average crystal size between about 0.5 micron and about 20 microns, such as between about 1 micron and about 10 microns, typically between about 1 micron and about 5 microns. After a predetermined sorption period, normally between about 0.1 and about 10 seconds, typically between about 0.1 and about 5 seconds, the para-xylene retained by the adsorbent is desorbed and collected to form a para-xylene enriched stream. When desorption cycle is complete, which typically takes between about 0.1 and about 10 seconds, generally between about 0.1 and about 5 seconds, the adsorption cycle is repeated. Thus the present process employs rapid cycle swing adsorption in that the time between successive sorption cycles is no more than 10 seconds, typically between about 0.2 and about 10 seconds, generally between about 0.2 and about 5 seconds.

Feedstock

The gaseous mixture fed to the present sorption separation process can be any $C_8$ aromatic product stream from a chemical plant or oil refinery, for example the $C_8$ fraction from a toluene disproportionation unit, a selective toluene disproportionation unit, a xylenes isomerization unit, or a reforming unit. Such a product stream generally comprises para-xylene, meta-xylene and ortho-xylene, as well as ethylbenzene, and may be fed directly to the sorption separation process or may initially be subjected to a xylene isomerization step to increase its para-xylene concentration. The gaseous feedstock from a selective toluene disproportionation unit could have a para-xylene concentration of above 80 wt %. In other cases, the gaseous feedstock to the present sorption separation process generally comprises:

| | |
|---|---|
| para-xylene | about 5 to about 25 wt %, |
| meta-xylene | about 40 to about 70 wt %, |
| ortho-xylene | about 5 to about 25 wt %, and |
| ethylbenzene | about 0 to about 25 wt %. |

In addition, the gaseous mixture may contain up to about 1 wt % hydrogen, which may be present in the mixture as a by-product of an earlier production step, such as reforming, or may be deliberately added to the mixture.

Sorption Separation

The separation process employed herein involves swing adsorption, which is a cyclic adsorption/desorption method of separating different components in a vapor or gas phase that relies on at least two of the components having different adsorption characteristics under the different conditions, particularly different pressures. However, other conditions, if beneficial, such as temperature may be changed during the desorption mode. The present separation process will be described with reference to a pressure swing adsorption (PSA) unit, but it is to be understood that this discussion also contemplates the use of a temperature swing adsorption (TSA) unit.

A PSA unit operates in adsorption mode-desorption mode cycles with a cycle time. In the adsorption mode, there may be a pressurization step and a high pressure adsorption step. The desorption mode may include (a) a blowdown step, either co-current or countercurrent, (b) a low-pressure desorption step and optionally, (c) prior to the blowdown step, a rinse step at high pressure (such as adsorption mode pressure) to purge the adsorbent bed for higher product purity. There may be additional steps such as pressure equalization in operating a PSA unit to reduce utility usage or to obtain better results. The cycle time may be constant or variable. There also may be one or more purges within or outside each regular PSA cycle. These purges are carried out as scheduled, as needed or both.

A PX-depleted effluent stream is produced during the adsorption mode of PSA. During the desorption mode of PSA, a desorption stream having an enriched PX concentration is produced. Optionally, as will be discussed below, the PX-depleted effluent stream from the PSA unit may be sent back to become part of the feedstream to an isomerization reactor. This effluent stream can also be used to purge the PSA sorbent bed to recover more PX trapped in voids of the sorbent after the desorption mode of the cycle. It is preferred to have at least two PSA sorbent beds, which may be operated under the same or different conditions.

As used herein, the term "PX-depleted" means that PX concentration is lowered in the effluent stream of a particular PSA unit compared to the concentration in the feedstream to the same PSA unit. It does not mean that all of PX has to be depleted or removed from the xylenes-containing feedstream(s) to the PSA unit(s). Typically, in the present process, the para-xylene-depleted effluent stream comprises between about 5 wt % and 80 wt % of the para-xylene contained in the gaseous $C_8$ aromatic mixture fed to the PSA unit.

In the adsorption mode, the gaseous feed is normally pressurized, typically to a pressure of between about 100 kPa absolute and about 1000 kPa absolute, and is then contacted with the adsorbent whereby the para-xylene, and normally at least part of any ethylbenzene, in the mixture is selectively adsorbed by the adsorbent. The preferential adsorption of PX partially or totally depletes the PX in the raffinate exiting the PSA unit during the adsorption mode of the cycle, thus effecting a desired partial or full separation between the selectively adsorbed component, PX, and the rest in the mixture.

The adsorption is continued for a predetermined time, between about 0.1 and about 10 seconds, such as between about 0.1 and about 5 seconds, or until the capacity of the adsorbent is reached, whichever occurs earlier. Depending on the component adsorbed, the type of separation and operational criteria defining a successful separation, the capacity of a particular adsorbent is considered to have been reached when one or more of the following is observed in the effluent: (a) PX is detected; (b) the concentration of PX becomes higher than a pre-determined acceptable level; and (c) the concentration of PX becomes the same as that in the feedstream.

After operating in the adsorption mode for a certain period of time or until the capacity of the adsorbent is reached, the PSA bed is switched to desorption mode and the flow of the $C_8$ aromatic feedstream is stopped or diverted to another PSA bed, or other suitable processing equipment in the plant. In the desorption mode, there is usually a blowdown step whereby the pressure of the PSA unit is lowered, followed by a low-pressure desorption step. Desorption of the preferentially adsorbed component, PX, may be effected by various ways such as depressurization, evacuation (to pressures lower than atmospheric pressures), low pressure stripping, or simple stripping. Depressurization (lowering the pressure) to desorb PX is preferred.

This desorption step is sometimes also referred to as the regeneration step, and once the adsorbent is "regenerated", the flow of the feedstream, is resumed for the adsorption mode unless a purge is performed. One or more purges of the PSA unit or other associated equipment using a different gas or liquid material, for example the PX-depleted effluent, between the adsorption and the desorption steps may be carried out for each cycle or as needed to avoid the build up of undesirable impurities. In the present process, the time period going through a complete adsorption-desorption cycle is referred to as the cycle time. The cycle time employed herein is very short, typically between about 0.2 and about 10 seconds, and generally less than 5 seconds.

The sorbent used in the present process comprises a crystalline molecular sieve capable of selectively adsorbing para-xylene, normally together with ethylbenzene, from a $C_8$ aromatic feedstream. Such a molecular sieve typically comprises at least one pore system defined by a ten-membered ring of tetrahedrally coordinated atoms. Examples of suitable molecular sieves include those having a structure type selected from MFI, MEL, TON, MTT, MFS, MWW, FER, EUO, AEL, ITH and AFO. Where the molecular sieve is an aluminosilicate, it is generally preferred that the silica to alumina molar ratio of the molecular sieve is between about 100 to about 500. One particularly preferred molecular sieve is ZSM-5 with crystals having either a spherical shape morphology or a coffin-shape morphology, or mixtures thereof.

One important factor in determining the effectiveness of the molecular sieve in the selective adsorption is the average size of the molecular sieve crystals. In particular, it is found that optimal separation efficiency, particularly with the medium pore molecular sieves generally employed herein, is achieved when the average crystal size of the molecular sieve is between about 1 micron and about 10 microns, typically between about 1 micron and about 5 microns.

The sorbent may be in the form of a structured sorbent, wherein the adsorbent and, optionally, a suitable heat absorbing medium, are placed on a structured supports such as a monolith. The support may be made from a large number of materials, such as silica, mullite, zirconia, alumina, titania, magnesia, metals such as steel and mixtures thereof. The support may be oriented or not oriented and support may be shaped as honeycomb, sponge, screens, or coils. The support also may be coated with other materials, such as colloidal silica spherulites. To the extent they disclose and describe such supports, U.S. Pat. Nos. 5,925,800 and 3,518,206 are incorporated herein by reference. Structured sorbents typically allow the use of very short adsorption-desorption cycles without very high pressure drops.

Where the adsorbent is present on a support, the total amount of adsorbent, together with optional heat absorbing medium, on the support is typically in the range of from about 0.01 wt % to 90 wt %, based on the weight of the support.

Because the adsorption mode is usually exothermic, it is sometimes advantageous to use an inert or substantially inert heat absorbing medium in the PSA unit. The heat absorbing medium may be gaseous, liquid, or solid but, in order to minimize downstream separation and product contamination problems, it is more convenient to use a solid heat absorbing medium. For example, aluminum particles may be mixed with the selected adsorbent(s) to form a suitable mixture to be placed in a PSA unit. Other such suitable solid media include, but are not necessarily limited to silicon carbide, carborundum, graphite, tungsten carbide, and mixtures thereof as well as with aluminum particles. These materials are typically inert to xylenes and ethylbenzene and possess high heat capacity and/or high thermal conductivity.

When a heat absorbing medium is used in the PSA unit, the amount thereof relative to that of the adsorbent itself is generally in the range of from about 100:1 to about 1:100, such as from about 1:10 to about 10:1, for example from about 1:9 to about 1:1, all by volume ratios. Using too little of a heat absorbing medium in the PSA unit would not impart sufficient desirable effects on heat management, heat transfer or temperature control. On the other hand, using too much of such a non-adsorbing material will necessarily decrease the capacity, thus the PX throughput, of a particular PSA unit on a volume basis because too much adsorbent is necessarily displaced. Otherwise, a much larger reactor may be needed at the expense of higher capital investment. It is also possible to employ an adsorbent support having beneficial heat absorbing properties.

The pressure swing adsorption step is operated in the vapor or gas phase. In order to maintain all or substantially all of the feedstock compounds in the vapor or gaseous phase, one having ordinary skill in the art understands that there is a general correlation between operating temperature and total/partial pressures of the compounds. In general, for a given mixture composition to be separated, the higher the sorbent bed temperature, the higher the available operating pressure. Higher pressures are generally preferred for the adsorption mode of the PSA unit.

A suitable temperature for the adsorption mode of the PSA unit is in the range of from about 150° C. to about 400° C., preferably from about 175° C. to about 300° C. Where the feedstock to the PSA unit is supplied by a xylene isomerization unit, it is preferred that the temperature in a PSA is no higher than that of the effluent from the isomerization reactor so that no additional heat input is needed. In some case, the isomerization effluent may have to go through a heat exchanger to lower its temperature. The pressure for the adsorption mode is generally in the range of from about 200 kPa absolute to about 20 MPa absolute, such as from about 300 kPa absolute to about 15 MPa absolute.

The desorption mode is carried out at a temperature in the range of from about 150° C. to about 550° C., such as from about 175° C. to about 400° C. The pressure in the desorption mode can be any value lower than the adsorption pressure, since there is usually a blowdown step to reduce the pressure after the adsorption is completed. A useful pressure range is from about 1 kPa absolute to about 1 MPa absolute, such as from about 10 kPa absolute to about 500 kPa absolute, for example from about 100 kPa absolute to about 200 kPa absolute.

Xylene Isomerization

The present swing adsorption process is normally used in combination with one or more xylene isomerization steps either to provide the gaseous feedstock to the adsorption process or the increase the para-xylene concentration of the PX-depleted effluent from the adsorption step or both. A large variety of xylene isomerization processes are known and any of these processes can be used with the present adsorption process. For example, it may be desirable to employ a xylene isomerization process that is effective to convert ethylbenzene in the $C_8$ aromatic feedstream to other compounds, such as by isomerization to xylenes or by cracking to benzene and a $C_2$ component. Examples of suitable xylene isomerization processes are disclosed in U.S. Pat. Nos. 4,899,011, 5,516, 946, 5,689,027, 6,028,238 and 6,924,405, the entire contents of which are incorporated herein by reference.

In one embodiment, each xylene isomerization step employed in the present process is conducted in the presence of at least two catalyst components, the first of which has the primary function of selectively deethylating the ethylbenzene in the feedstream to benzene, while the second catalyst component selectively isomerizes xylenes in the feed. The first catalyst component can, and preferably will, effect some isomerization of the xylenes in the feed.

Each of the first and second catalyst components comprises an intermediate pore size molecular sieve which is characterized by a Constraint Index within the approximate range of 1 to 12 (e.g., less than about 7 Angstroms pore size, such as from about 5 to less than about 7 Angstroms). The method by which Constraint Index is determined is described fully in U.S. Pat. No. 4,016,218, incorporated herein by reference for details of the method. Examples of intermediate pore size molecular sieves useful in the present process include ZSM-5 (U.S. Pat. Nos. 3,702,886 and Re. 29,948); ZSM-11 (U.S. Pat. No. 3,709,979); ZSM-12 (U.S. Pat. No. 3,832,449), ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein.

The molecular sieve of each of the first and second catalyst components is preferably associated with a hydrogenation-dehydrogenation component. Examples of such components include the oxide, hydroxide, sulfide, or free metal (i.e., zero valent) forms of Group 8 to 10 metals (i.e., Pt, Pd, Ir, Rh, Os, Ru, Ni, Co and Fe), Group 6 metals (i.e, Cr, Mo, W), Group 14 metals (i.e., Sn and Pb), Group 15 metals (i.e., Sb and Bi), and Group 7 metals (i.e., Mn, Tc and Re). As used herein, the new numbering scheme for the Periodic Table Groups are as disclosed in Chemical and Engineering News, 63(5), 27 (1985). Combinations of catalytic forms of such noble or non-noble metal, such as combinations of Pt with Sn, may be used. The metal is preferably in a reduced valence state, e.g., when this component is in the form of an oxide or hydroxide. The reduced valence state of the metal may be attained, in situ, during the course of a reaction, when a reducing agent, such as hydrogen, is included in the feed to the reaction. In one preferred embodiment, the hydrogenation-dehydrogenation component is a noble metal (i.e., Pt, Pd, Ir, Rh, Os and Ru) and most preferably is platinum. In a further preferred embodiment, the hydrogenation-dehydrogenation component is an early transition metal, such as molybdenum, tungsten, rhenium and/or manganese, typically rhenium.

Each of the components of the catalyst system will normally exhibit mutually exclusive xylene diffusional properties. These properties can be identified by noting the time (in minutes) required to sorb 30% of the equilibrium capacity of ortho-xylene at 120° C. and at an ortho-xylene partial pressure of 600±107 Pa (4.5±0.8 mm of mercury), a test described in U.S. Pat. Nos. 4,117,026; 4,159,282; and Re. 31,782; each of which is incorporated by reference herein. The equilibrium capacity of ortho-xylene is defined herein as greater than 1 gram of xylene(s) per 100 grams of molecular sieve. In the catalyst system, the first catalyst component effective for ethylbenzene conversion typically has an ortho-xylene sorption time (in minutes) in excess of about 50 minutes, such as greater than about 1200 minutes, but normally less than 10,000 minutes, while on the other hand, the second, isomerization component typically has an ortho-xylene sorption time of less than about 50 minutes, such as less than about 10 minutes.

The desired xylene diffusion properties of the first catalyst component can be achieved in a number of ways. For ortho-xylene diffusion times at or near the minimum value of 50 minutes, the selection of a large crystal form of the molecular sieve used in the catalyst, that is having an average crystal size in excess of 1 micron, may be sufficient. However, to achieve higher diffusivity values, it may be desirable to selectivate the first catalyst component by deposition on the surface of the catalyst particles of a layer of coke and/or an oxide, such as silica, which is inert under the process conditions experienced in use. Where the catalyst particles are selectivated, both large crystal size and medium crystal size (having a crystal size of 0.2-0.5 micron) molecular sieves can be used in the first catalyst component. Where the first catalyst component is to be selectivated with silica, this is conveniently achieved by subjecting the catalyst to one or more treatments with an organosilicon compound in a liquid carrier, each treatment being followed by calcination of the treated material in an oxygen containing atmosphere, e.g., air. Such a multiple selectivation procedure is described in U.S. Pat. No. 5,476, 823, the entire contents of which are incorporated herein by reference.

The second catalyst component, which is effective to isomerize xylenes, preferably has an ortho-xylene sorption time of less than about 50 minutes and preferably less than about 10 minutes. This is typically achieved by using a small crystal size molecular sieve, having an average crystal size of 0.02-0.05 micron, in this component. The molecular sieve of the second component of the catalyst system will typically have an alpha value less than about less than 50 and preferably from about 5 to about 25.

In general, the xylene isomerization step is carried out in a fixed bed reactor containing the catalyst system described above. In one embodiment, the first and second components of the catalyst system are in sequential beds in a single reactor. That is, the component of the catalyst system used in the process of the invention which is effective for ethylbenzene conversion forms a first bed, while the other component of the catalyst system, which is effective for xylene isomerization, forms a second bed downstream of the first bed. The feed is typically cascaded from the first to the second bed without intervening separation of light gases. As an alternative, the first and second beds could be disposed in separate reactors which, if desired, could be operated at different process conditions.

The conditions used in the xylene isomerization step are not narrowly defined, but generally will include a temperature of from about 200° C. to about 540° C., a pressure of from about 0 to about 1,000 psig (100 to 7000 kPa), a weight hourly space velocity (WHSV) of between about 0.1 and about 200 $hr^{-1}$, and a hydrogen, $H_2$, to hydrocarbon, HC, molar ratio of between about 0.2 and about 10. Preferably, the conditions include a temperature of from about 340° C. to about 450° C., a pressure of from about 50 and about 400 psig (445 and 2860 kPa), a WHSV of between about 3 and about 50 $hr^{-1}$ and a $H_2$ to HC molar ratio of between about 1 and about 5.

Referring now to the drawings, one embodiment of the present process is shown in FIG. 1 in which a $C_8$+ aromatic mixture 11, such as from a reformer (not shown), is fed to a distillation column 12 to remove $C_9$+ components as a bottoms stream 13 and produce a $C_8$ overhead fraction 14. It is to be appreciated that references herein to a $C_n$+ aromatic stream are intended to mean that the stream is composed of aromatic hydrocarbons containing n or more carbon atoms.

The $C_8$ fraction 14 is then passed to a PX separation unit 15, which can be a crystallizer, a membrane separation unit or a sorption separation unit such as a PAREX™, ELUXYL™ or crystallization unit. The separation unit 15 removes para-xylene from the $C_8$ fraction 14 as a product stream 16 to leave a first PX-depleted stream 17. The stream 17 is then fed to a first xylene isomerization unit 18, where xylenes in the stream 17 are isomerized back towards equilibrium levels and optionally ethylbenzene in the stream 17 is converted to xylenes. As a result, the effluent 19 from the unit 18 contains para-xylene at or near equilibrium concentration and is then fed to a rapid cycle pressure swing adsorption unit 21 of the type described above.

During its adsorption cycles, the unit 21 preferentially adsorbs para-xylene from the effluent 19 to produce a second PX-depleted stream 22 which is then fed to a second xylene isomerization unit 23, where xylenes in the stream 22 are isomerized back towards equilibrium levels and again ethylbenzene may be converted to xylenes. Thus the effluent 24 from the unit 23 contains para-xylene at or near equilibrium concentration.

During the desorption cycles of the unit 21, the para-xylene adsorbed during the preceding adsorption cycles is released to produce a PX-rich stream 25, which is combined with the effluent 24 and fed to the distillation column 12 with the $C_8$+ aromatic mixture 11.

Figure 2:
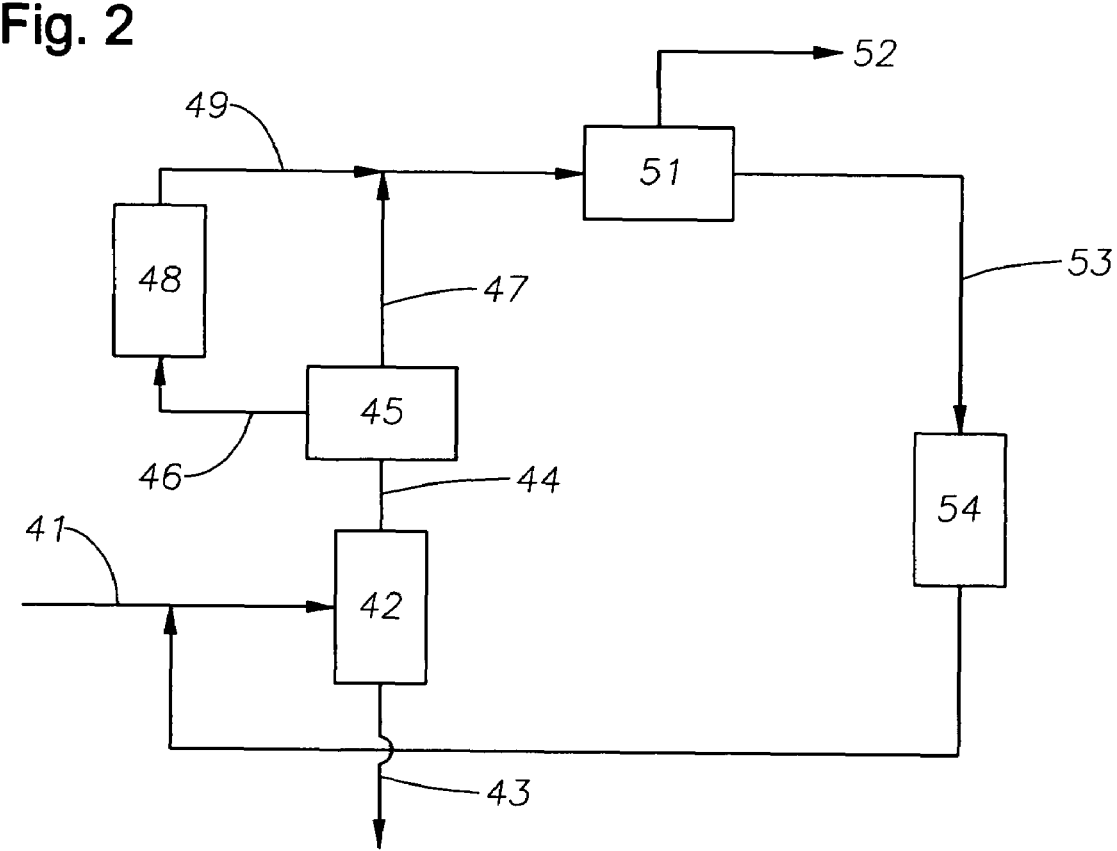
FIG. 2 is a flow diagram of a para-xylene production process according to a further embodiment of the present invention.

A further embodiment of the invention is shown in FIG. 2, in which, as in the preceding embodiment, a $C_8$+ aromatic mixture 41 is fed to a distillation column 42, such as a distillation column, to remove $C_9$+ components as a bottoms stream 43 and produce a $C_8$ overhead fraction 44. However, in the further embodiment, the $C_8$ overhead fraction 44 is fed to directly a rapid cycle pressure swing adsorption unit 45 of the type described above. During its adsorption cycles the unit 45 removes para-xylene from the fraction 44 to produce a PX-depleted stream 46 and during its desorption cycles the unit 45 the adsorbed para-xylene is released as a PX-rich stream 47.

The PX-depleted stream 46 is then passed to a xylene isomerization unit 48, where the xylenes in the stream 48 are isomerized back towards equilibrium levels and ethylbenzene may be converted to xylenes. The effluent 49 from the xylene isomerization unit 48 is then combined with the PX-rich stream 47 and the combined stream is fed to a PX separation unit 51, which can be a crystallizer, a membrane separation unit or a sorption separation unit such as a PAREX™, ELUXYL™ or crystallization unit. The separation unit 51 removes para-xylene from the combined stream 47, 49 as a product stream 52 to leave a further PX-depleted stream 53. The stream 53 is then passed through a further xylene isomerization unit 54 before being recycled to the splitter 42. In one embodiment, the separation unit 51 is a swing adsorption unit in which the cycle time between successive adsorption-desorption cycles is greater than 10 seconds.

The invention will now be more particularly described with reference to the accompanying Examples.

Example 1

Figure 3:
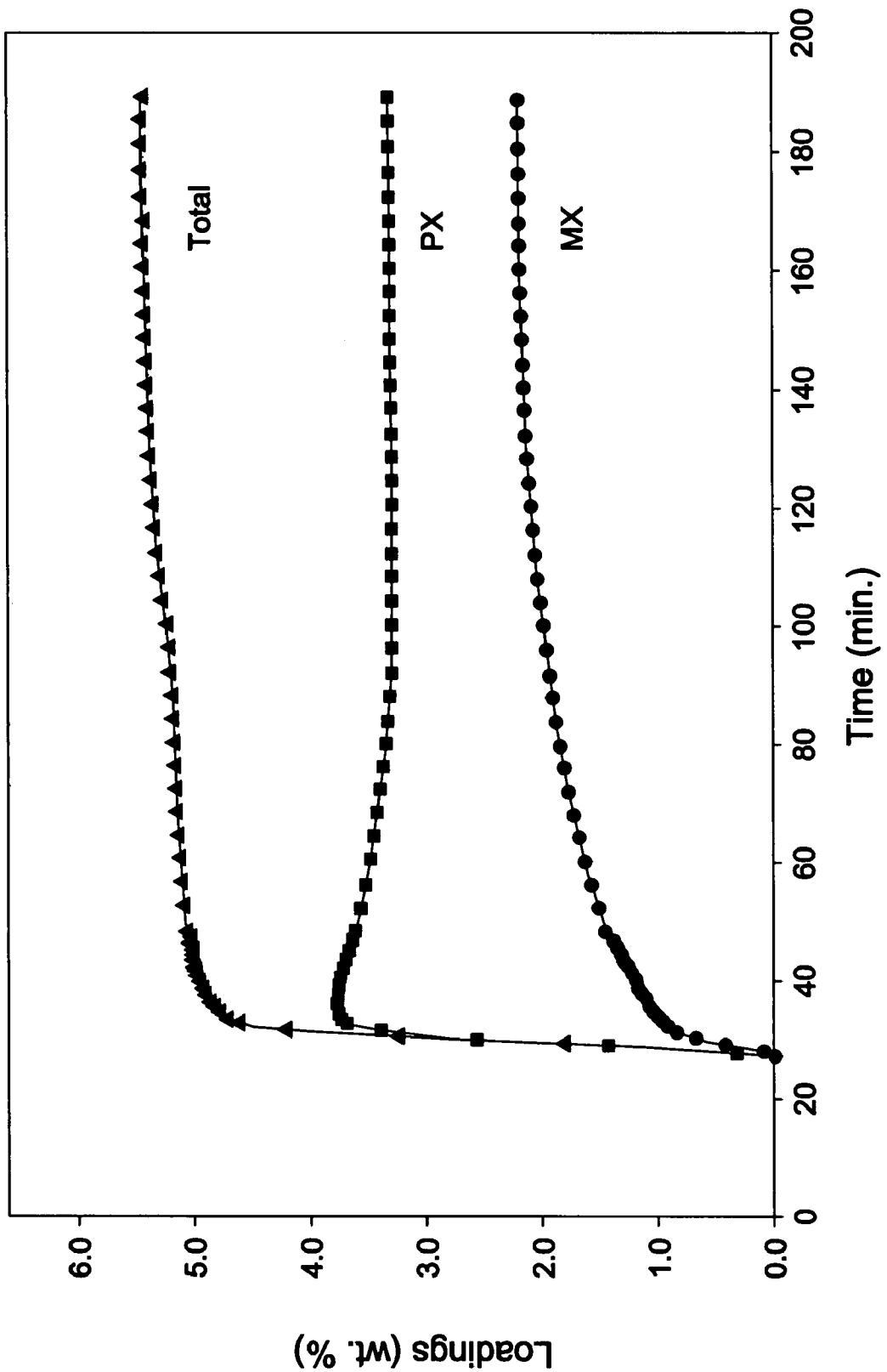
FIG. 3 compares the rates of adsorption of meta-xylene and para-xylene at a temperature of 250° C. and a pressure of 67 psia (462 kPa) for the molecular sieve of Example 1.

This example illustrates the selective adsorption properties of a silica-bound MFI zeolite (silica to alumina molar ratio 300) for para-xylene. The feed was a mixture of 49.5 wt % PX, 49.5 wt % MX and 1 wt % of 1,3,5-trimethylbenzene (TMB). The TMB was used as a reference since it was too bulky to enter the zeolite pores. The experiment was conducted in the vapor phase at a temperature of 250° C. and a pressure of 67 psia (462 kPa). The adsorbent was in the form of 60/80 mesh particles and was packed in a 5 cc stainless steel column. The feed was passed through the column and breakthrough was monitored to measure the adsorption rate and capacity. The results are presented in FIG. 3, from which it will be seen that the adsorbent showed a much higher capacity for PX than MX at breakthrough, indicating a more favorable kinetic environment for molecular transport of PX over MX. In addition, the adsorbent showed a significantly higher equilibrium adsorption capacity for PX (3.3 wt %) than for MX (2.2 wt %).

Example 2

Figure 4:
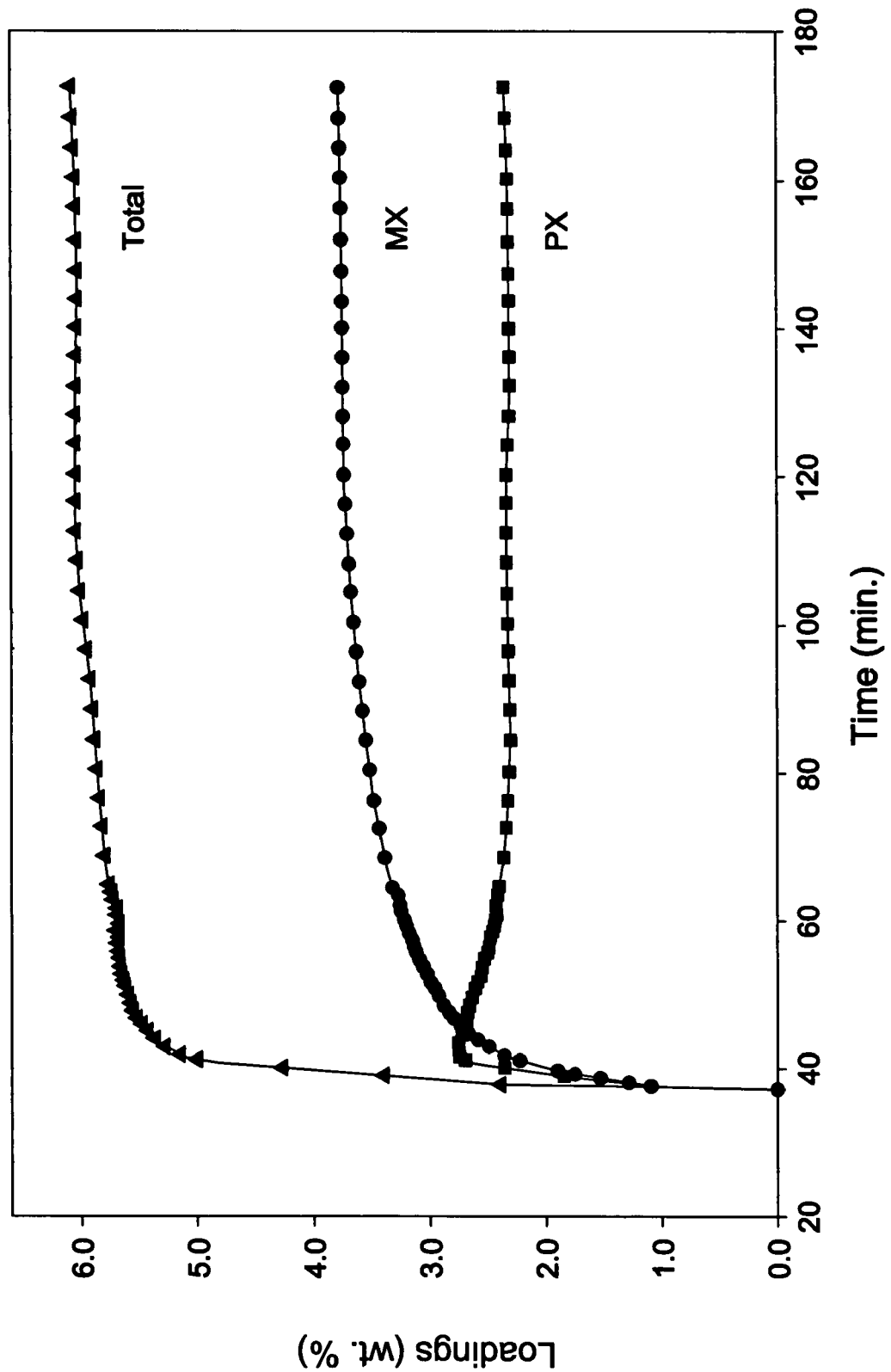
FIG. 4 compares the rates of adsorption of meta-xylene and para-xylene at a temperature of 252° C. and a pressure of 65 psia (448 kPa) for the molecular sieve of Example 2.

The process of Example 1 was repeated with a silica-bound MFI zeolite having a silica to alumina molar ratio greater than 500. The experiment was conducted in the vapor phase at a temperature of 252° C. and a pressure of 65 psia (448 kPa). The results are presented in FIG. 4, from which it will be seen that, although the high silica zeolite showed slightly preferential adsorption for PX over MX at breakthrough, this advantage was more than offset by an increased equilibrium adsorption capacity for MX (3.7 wt %) over PX (2.3 wt %).

Examples 3 to 23

A series of experiments were conducted to measure the adsorption uptakes for PX, MX, and OX of a series of highly siliceous MFI samples covering a wide range of crystal sizes between about 0.5 μm up to greater than 100 μm. The crystal size and silica to alumina molar ratio of each sample is summarized in Table 1.

TABLE 1

| Example | SiO$_2$/Al$_2$O$_3$ Ratio | Cation Type | Nominal Crystal Size |
|---|---|---|---|
| 3 | 50-100 | Na | 0.4 |
| 4 | 250 | Na | 0.5 |
| 5 | 1000 | Na | 0.5 |
| 6 | 260 | H | 0.7 |
| 7 | 260 | Na | 0.7 |
| 8 | >300 | Na | 15 |
| 9 | >300 | Na | 25 |
| 10 | >300 | Na | 45 |
| 11 | >300 | Na | 120 |
| 12 | 200 | H | 0.3 |
| 13 | 400 | H | 0.3 |
| 14 | 600 | H | 0.3 |
| 15 | 800 | H | 0.3 |
| 16 | 200 | Na | 0.3 |
| 17 | 400 | Na | 0.3 |
| 18 | 600 | Na | 0.3 |
| 19 | 800 | Na | 0.3 |
| 20 | 70 | Na | 1.25 |
| 21 | 70 | Na | 2 |
| 22 | 200 | Na | 2 |
| 23 | 200 | H | 2 |

Figure 5B:
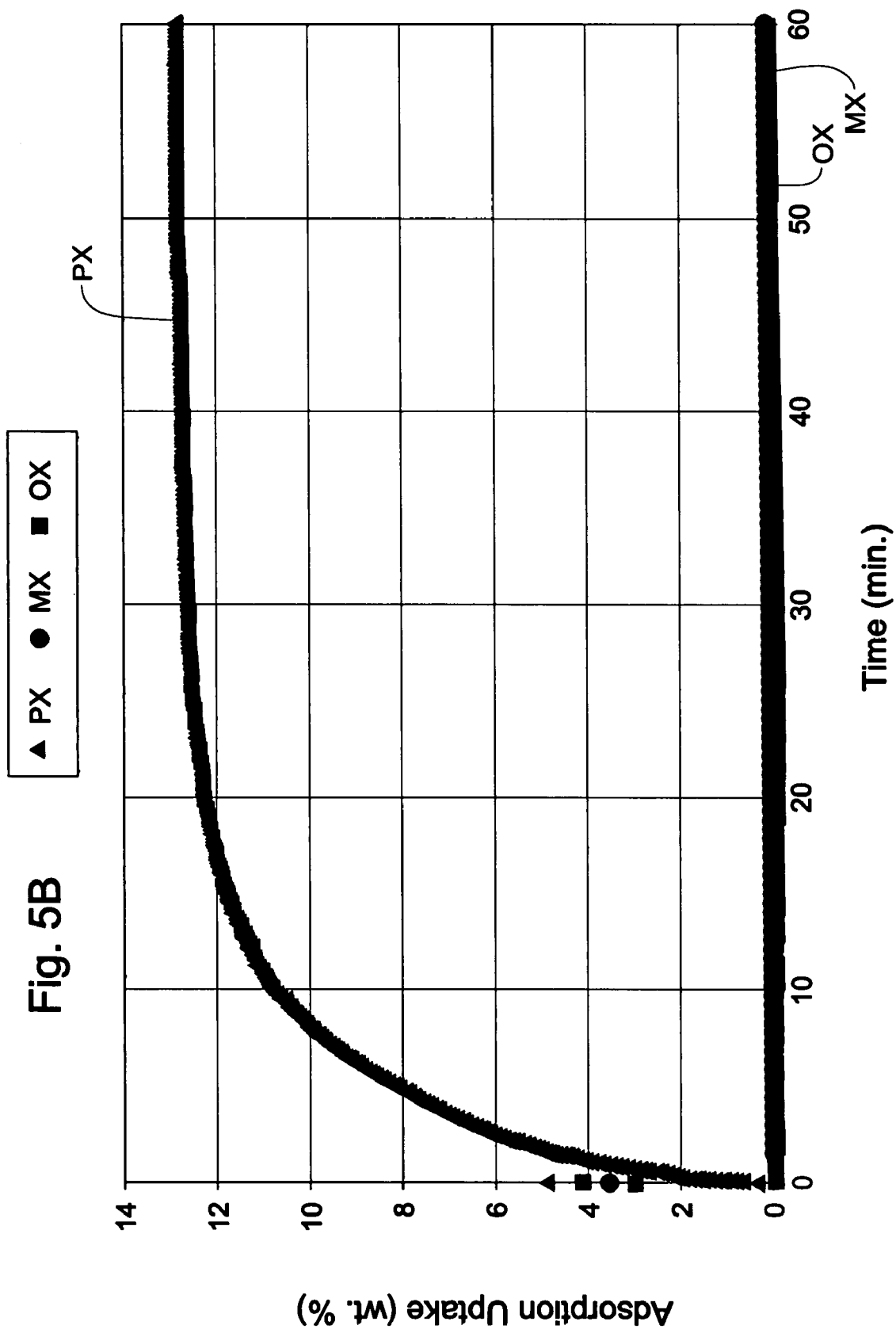
FIGS. 5(a) and (b) compare the gravimetric adsorption uptake of meta-xylene, ortho-xylene and para-xylene for the molecular sieves of Examples 4 and 8, respectively.

The experiments were conducted gravimetrically at 28° C. and 200 Pa (1.5 Torr) in a Cahn™ microbalance apparatus. Prior to contacting the samples with each of the individual isomers, the samples were evacuated for 16 hours at 400° C. This gave ample time for the removal of moisture and impurities from the samples. Upon admitting the isomers into the adsorption cell, the weight percent gain was monitored as a function of time for a period of 60 minutes. Good reproducibility of results was found by repeating some of the experiments. FIGS. 5(a) and (b) shows typical adsorption uptakes for a small crystal material (Example 4) and large crystal material (Example 8), respectively. The uptakes in all the small and large crystals followed similar trends to those in FIG. 5.

Consistent with the high crystallinity of the samples, it was verified that PX adsorption uptakes readily approach a saturation capacity of about 12-13 wt %, which translates to the expected loading of about 7-8 molecules per unit cell. The shape of the uptake curves follow the classical diffusion behavior that is expected for this type of experiment. The smaller crystals achieve PX saturation levels at a much shorter time than the larger crystals. Both small and large crystals, however, show low MX and OX uptakes even after 1 hour and therefore corresponding PX/MX and PX/OX selectivities are high. The short time behavior, however, is very different for small and large crystals. The small crystals undergo a nearly instantaneous rise in the adsorption uptake and then a gradual diffusion-like increase. The large crystals, on the other hand, display almost exclusively a diffusion-like behavior. This is consistent with the much larger contribution of external adsorption sites on the small crystals (i.e., much larger surface-to-volume ratio). Overall, the results of FIG. 5 clearly capture the expected interplay of PX selectivity and time response for small and large crystals. Although these scoping experiments are carried out at conditions of pressure and temperature that are far from those of a potential xylene separation process, the trends illustrated here are expected to hold at higher temperatures and pressures.

Figure 6A:
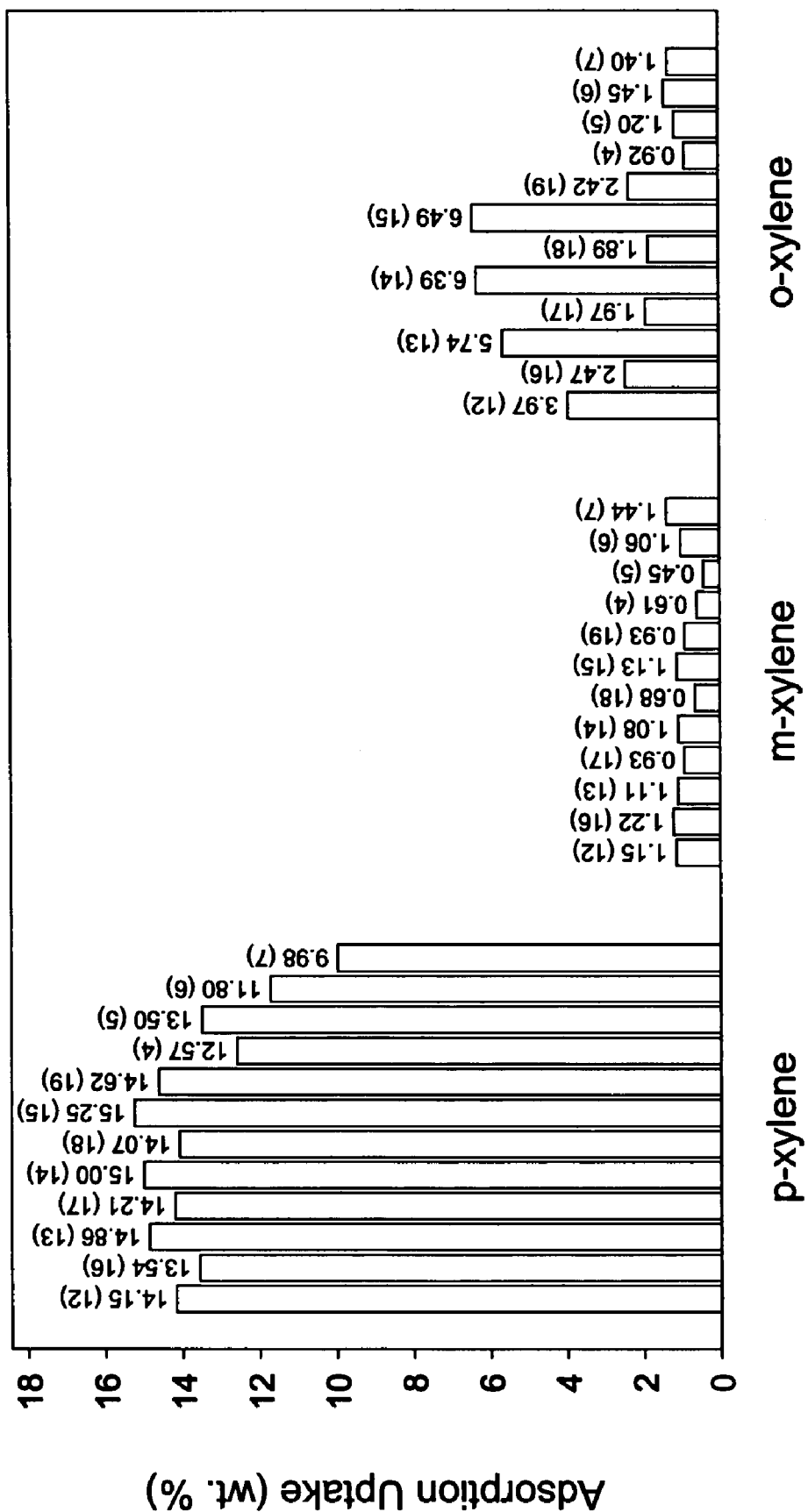
FIGS. 6(a) and (b) compare the adsorption uptake of meta-xylene, ortho-xylene and para-xylene after 1 hour at 28° C. for the molecular sieves of Examples 4 to 23.

FIGS. 6(a) and (b) summarize the adsorption uptakes after 1 hour for all the samples. FIG. 6(a) displays the results for the small crystals of Examples 4 to 7 and 12 to 19, whereas FIG. 6(b) displays the results for the large crystals of Examples 8 to 11 and 20 to 23. The small crystals consistently achieve higher MX and OX uptakes than the larger crystals and consequently exhibit lower PX/MX.

By making use of some simplifying assumptions on crystal morphology and the geometric arrangement in which MX or OX adsorb onto the external surface, it is possible to develop a simple theoretical equation to quantify the role of the surface-to-volume ratio on PX selectivity. This is done by dividing the number of PX molecules that adsorb within the crystals by the number of MX or OX molecules that adsorb onto the surface. As shown in detail in by the following equations, the PX selectivity is proportional to the inverse of the surface-to-volume ratio:

$$PX\ \text{selectivity} = \frac{PX\ \text{molecules with crystals}}{MX\ \text{or}\ OX\ \text{molecules on external surface}}$$

$$= \frac{(a^3/V_{uc} \times 10^{12})N_{uc}}{An}$$

where

MFI unit cell volume=$V_{uc}$=5211.28×10$^{-24}$ cm$^3$

MFI crystal density=$\rho$=1.84 g/cm

PX molecular weight=MW=106 g/mole

Avogadro's number=$N_{av}$=6.02×10$^{23}$ molecules/mole

PX saturation loading=$W_o$=0.13 g/g

PX molecules per unit cell=$N_{uc}=W_o \rho V_{uc} N_{av}$/MW

Nominal crystal size=$\alpha \mu$m

Crystal aspect ratio (parallel piped)=$\alpha$=2

Crystal volume=$(a)(a/\alpha)(a\alpha)=a^3 \mu m^3$

External surface of crystal=$A=2a^2(1+\alpha+1/\alpha)$

MX or OX molecular diameter=$d$=5.8×10$^{-4}$ mm

MX or OX surface packing density=$(1-\epsilon)$=0.6

MX or OX molecules/unit surface=$n=4(1-\epsilon)/\pi d^2$

MX or OX molecules on external surface=$An$

Figure 7:
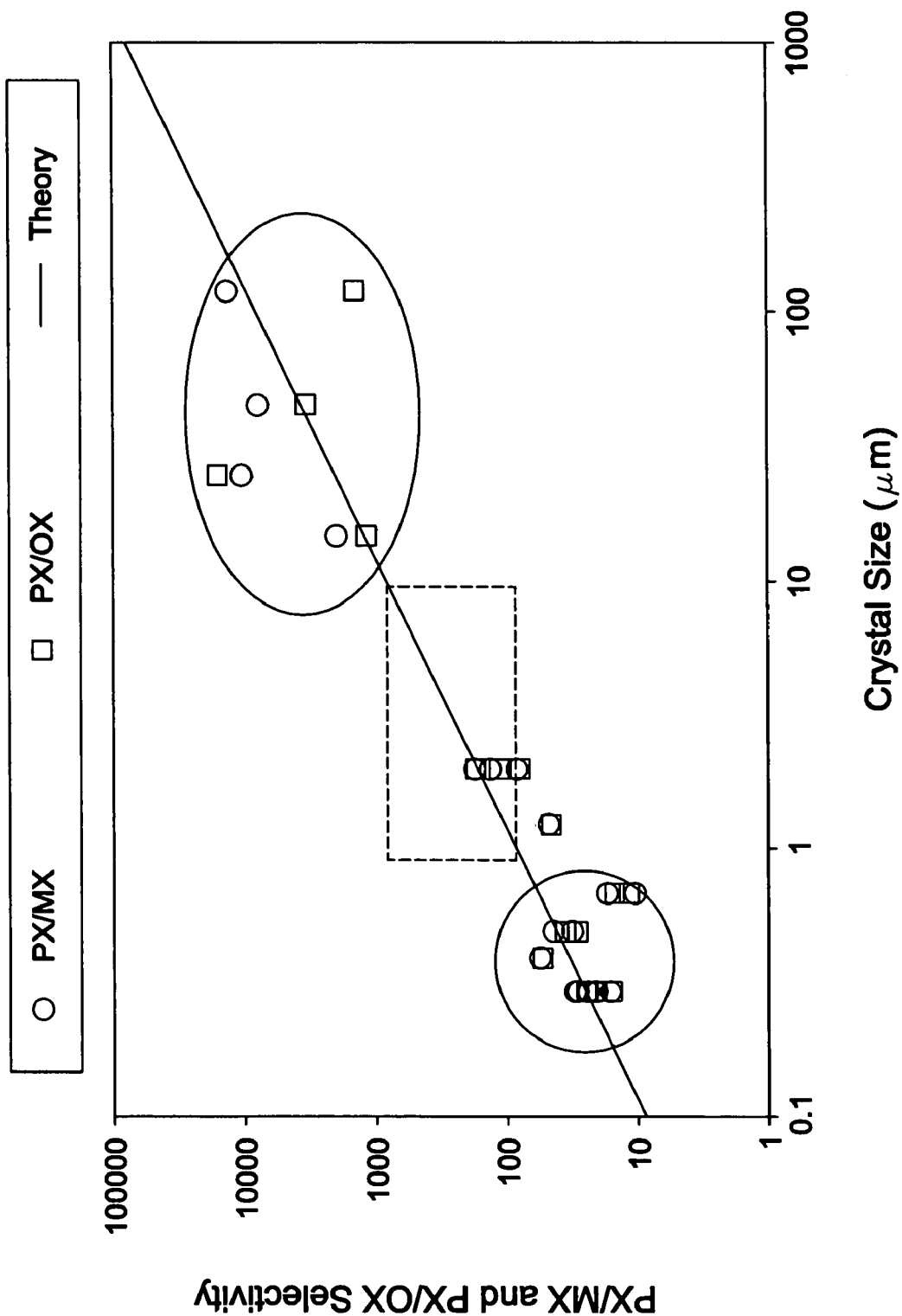
FIG. 7 is a graph plotting calculated and measured PX selectivity against crystal size for the MFI molecular sieves of Examples 4 to 23.

The PX selectivity can also be directly calculated from the experimental data such as shown in FIG. 5. In order to calculate the PX/MX and PX/OX selectivity the following procedure can be used: (a) for the small crystals the PX uptake at 1 hour is divided by the instantaneous MX and OX uptake and (b) for the large crystals the PX uptake at 1 hour divided by the MX and OX uptake at an early time (0.2 to 0.4 sec). As shown in FIG. 5, the absence of a steady uptake value at early times required a procedure such as (b). By these choices, the diffusion-like uptake contribution for both small and large crystals can be removed. The results of the theoretical and experimental selectivities thus calculated are plotted in FIG. 7, in which the solid line corresponds to the theoretical calculated PX selectivity, whereas the symbols correspond to the data. There is a clear segregation in PX selectivities for small and large crystals (circular and oval regions, respectively). The small crystals lead to low PX selectivities, whereas the large crystals lead to high selectivities. The expected diffusion time scale, on the other hand, increases with the square of the characteristic diffusion distance in the crystals, rendering the very large crystals inadequate for swing adsorption with rapid cycle times. Thus, there is an intermediate region of MFI crystal sizes (between about 1 micron and about 10 microns) represented by the dotted rectangle that optimally meets the conditions of high PX selectivity and short response time for use in swing adsorption with rapid cycle times.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing a para-xylene enriched product from a gaseous mixture comprising at least para-xylene, meta-xylene and ortho-xylene, the process comprising:
   (a) contacting the gaseous mixture with an adsorbent capable of selectively adsorbing para-xylene and comprising a crystalline molecular sieve having an average crystal size between about 0.5 micron and about 20 microns, said contacting being conducted at a temperature and pressure such that at least part of the para-xylene in the mixture is adsorbed by the adsorbent to produce a para-xylene-depleted effluent stream; then
   (b) desorbing para-xylene from said adsorbent;
   (c) collecting the desorbed para-xylene to form a para-xylene enriched stream; and
   (d) repeating (a) and (b) for a plurality of cycles, wherein the time between successive contacting steps is no more than 10 seconds.

2. The process of claim 1 wherein the crystalline molecular sieve has an average crystal size between about 1 micron and about 10 microns.

3. The process of claim 1 wherein the crystalline molecular sieve comprises at least one pore system defined by a ten-membered ring of tetrahedrally coordinated atoms.

4. The process of claim 1 wherein the crystalline molecular sieve comprises a material having a structure type selected from MFI, MEL, TON, MTT, MFS, MWW, FER, EUO, AEL, ITH and AFO.

5. The process of claim 1 wherein the crystalline molecular sieve comprises an aluminosilicate having a silica to alumina molar ratio of 100 to 500.

6. The process of claim 5 wherein the crystalline molecular sieve comprises an MFI structure-type molecular sieve.

7. The process of claim 6 wherein the MFI molecular sieve comprises a crystal morphology of spherical shape, coffin shape, or mixture thereof.

8. The process of claim 1 wherein para-xylene is desorbed from said adsorbent by decreasing the partial pressure of para-xylene.

9. The process of claim 1 wherein the time between successive contacting steps is between about 0.2 and about 10 seconds.

10. The process of claim 1 wherein the time between successive contacting steps is between about 0.2 and about 5 seconds.

11. The process of claim 1 wherein said para-xylene-depleted effluent stream comprises between about 5 wt % and about 80 wt % of the para-xylene contained in said gaseous mixture.

12. The process of claim 1 wherein at least part of the para-xylene-depleted effluent stream is passed to a xylene isomerization unit to increase the para-xylene content thereof and produce a second effluent stream.

13. The process of claim 12 wherein at least part of the para-xylene enriched stream and/or the second effluent stream is subjected to a further para-xylene separation step.

14. The process of claim 13 wherein said further para-xylene separation step comprises selective crystallization, membrane separation and/or selective adsorption.

15. The process of claim 14 wherein said further para-xylene separation step comprises:
   (a) contacting the stream with a further adsorbent capable of selectively adsorbing para-xylene such that at least part of the para-xylene in the stream is adsorbed by the adsorbent to produce a further para-xylene-depleted effluent stream; then
   (b) desorbing para-xylene from said further adsorbent;
   (c) collecting the desorbed para-xylene to form a further para-xylene enriched stream; and
   (d) repeating (a) and (b) for a plurality of cycles, wherein the time between successive contacting steps is greater than 10 seconds.

16. The process of claim 15 wherein the further para-xylene-depleted effluent stream is passed to a further xylene isomerization unit to increase the para-xylene content thereof and produce a third effluent stream.

17. The process of claim 15 wherein said gaseous mixture comprises at least part of the third effluent stream.

* * * * *